(12) United States Patent
Buisan Ferrer et al.

(10) Patent No.: US 12,310,664 B2
(45) Date of Patent: May 27, 2025

(54) HANDHELD AESTHESIOMETER

(71) Applicant: BRILL ENGINES, S.L., Barcelona (ES)

(72) Inventors: José Buisan Ferrer, Barcelona (ES); Laurent David Valat, Barcelona (ES); Laura Nieto Cavia, Barcelona (ES)

(73) Assignee: BRILL ENGINES, S.L., Barcelona (ES)

( * ) Notice: Subject to any disclaimer, the term of this patent is extended or adjusted under 35 U.S.C. 154(b) by 875 days.

(21) Appl. No.: 17/252,925

(22) PCT Filed: Jun. 5, 2019

(86) PCT No.: PCT/ES2019/070386
§ 371 (c)(1),
(2) Date: Dec. 16, 2020

(87) PCT Pub. No.: WO2019/243646
PCT Pub. Date: Dec. 26, 2019

(65) Prior Publication Data
US 2021/0259547 A1    Aug. 26, 2021

(30) Foreign Application Priority Data
Jun. 18, 2018   (EP) .................................... 18382436

(51) Int. Cl.
*A61B 3/16*    (2006.01)
*A61B 5/00*    (2006.01)

(52) U.S. Cl.
CPC ............ *A61B 3/165* (2013.01); *A61B 5/4827* (2013.01); *A61B 5/7405* (2013.01); *A61B 5/742* (2013.01); *A61B 2560/0431* (2013.01)

(58) Field of Classification Search
CPC ......... A61B 3/16; A61B 3/165; A61B 5/4827; A61B 5/7405; A61B 5/742; A61B 2560/0431; A61B 3/00; A61B 3/18
See application file for complete search history.

(56) References Cited

U.S. PATENT DOCUMENTS 3,470,736 A    10/1969   Bartfay
4,770,181 A    9/1988    Tomoda
(Continued)

FOREIGN PATENT DOCUMENTS

CN       203539330 U    4/2014
WO       93/17613 A2    9/1993
(Continued)

OTHER PUBLICATIONS

International Search Report of PCT/ES2019/070386 dated Oct. 7, 2019 [PCT/ISA/210].
European Search Report of EP 18 38 2436.6 dated Nov. 23, 1018.

*Primary Examiner* — Charles A Marmor, II
*Assistant Examiner* — Severo Antonio P Lopez
(74) *Attorney, Agent, or Firm* — Sughrue Mion, PLLC (57) ABSTRACT

The invention relates to a handheld aesthesiometer, comprising a gas lung connected with intermediation from first valve means to a source of gas and comprising an expandable cavity intended to house a volume of gas in a loading phase of the aesthesiometer; an outlet nozzle connected to the gas lung with intermediation from second valve means and suitable for directing a puff of the volume of the gas housed in the gas lung in a firing phase of the aesthesiometer; and a mechanism to ensure in the aforementioned firing phase of the aesthesiometer the release of the puff of the volume of gas contained in the gas lung in the direction of the outlet nozzle by means of a controlled contraction of the (Continued)

expandable cavity of the gas lung in order to ensure a substantially constant outlet pressure.

16 Claims, 6 Drawing Sheets

(56) References Cited

U.S. PATENT DOCUMENTS

| | | | | |
|---|---|---|---|---|
| 5,048,526 A | * | 9/1991 | Tomoda | A61B 3/165 600/401 |
| 5,299,573 A | * | 4/1994 | Kobayashi | A61B 3/165 600/401 |
| 5,997,518 A | * | 12/1999 | Laibovitz | A61F 9/0008 604/296 |
| 6,355,003 B1 | * | 3/2002 | Aviv | A61B 5/03 600/560 |
| 2002/0103427 A1 | * | 8/2002 | Miwa | A61B 3/16 600/401 |
| 2014/0316233 A1 | * | 10/2014 | Akiba | A61B 3/165 600/401 |
| 2019/0128720 A1 | * | 5/2019 | Farrell | G01F 3/20 |

FOREIGN PATENT DOCUMENTS

| | | |
|---|---|---|
| WO | 94/12104 A1 | 6/1994 |
| WO | 2018/017594 A1 | 1/2018 |

* cited by examiner

HANDHELD AESTHESIOMETER

CROSS REFERENCE TO RELATED APPLICATIONS

This application is a National Stage of International Application No. PCT/ES2019/070386 filed on Jun. 5, 2019, claiming priority based on European Patent Application No. 18382436.6 filed on Jun. 18, 2018.

TECHNICAL FIELD OF THE INVENTION

The invention relates to a handheld aesthesiometer prepared to produce puffs of air at different intensity levels that are suitable for measuring the tactile sensation in the cornea of a patient.

BACKGROUND OF THE INVENTION

Aesthesiometry is the measurement of sensation, especially tactile sensation.

Corneal aesthesiometry is generally used clinically to evaluate neurotrophic keratitis. Neurotrophic keratitis, also known by its initials NK, is a degenerative disease of the cornea produced by damage in the trigeminal nerve that causes a loss of corneal sensitivity, the development of spontaneous wounds in the corneal epithelium and the degradation of the ability to heal, which can result in the development of ulcers, aseptic necrosis and perforation in the cornea. Cornea sensitivity is a condition that can also affect patient with diabetes, ocular herpes, contact lens users and some types of dry eyes.

In research, aesthesiometry has been used with different aims, such as for example for recording the duration of painkillers in the cornea.

There exist qualitative and quantitative methods to evaluate corneal sensation. The most common quantitative method is carried out with the handheld Cochet-Bonnet aesthesiometer which has a nylon monofilament that rests on the corneal surface just enough to cause it to curve. Said filament will exert more pressure the shorter it is. The examination is started with the filament extended and it gets shorter until obtaining a response from the patient.

The technique using puffs of air without contact is also known. Nevertheless, the instruments known until now for applying this technique do not enable the use of handheld aesthesiometers.

The first reference known of an aesthesiometer with puffs of air is patent document WO 9412104 which describes a method that comprises applying to the cornea or conjunctiva of the eye, whose sensitivity is to be determined, a flow of gas which contains a mixture of $CO_2$ and air in variable concentrations, or an acid isotonic solution; and carrying out qualitative or quantitative aesthesiometry of the local irritation produced by the application of the irritating product, based on determining the pain threshold and intensity, through oral answers or the use of a logic scale.

The equipment proposed for the implementation of the method comprises a $CO_2$ cylinder and an air cylinder; a gas-mixing device; a gas flow indicator; a pressure transducer; an oscilloscope; a valve; a pulse generator; a universal lens support for supporting a tube for expelling the gas mixture.

In practice, this equipment creates a continuous flow of the gas mixture and by means of a three-outlet valve the flow is directed towards the tube for expelling that is focused on the eye of the patient. The appropriate flow is achieved by means of a flow regulator, arranged upstream from the three-outlet valve that, with the experimental data or by means of the incorporation of a pressure transducer in the equipment, the equivalent pressure of the gas mixture is estimated.

The equipment described, including the flow regulator and the pressure transducer, is not apt for miniaturisation, at least to the extent to which it can be a handheld, self-supporting device that can be gripped by a doctor.

Patent documents WO 201817594 and WO 9317613 describe alternate equipment for an aesthesiometer that uses the puff technique, but are not apt to be miniaturised.

In patent document WO 201817594 equipment is proposed in which the firing is actuated with a pedal and in which a pressure regulator and several components intervene in order to produce puffs of gas at an objective pressure for a duration of 2 s.

Patent document WO 9317613 proposes connecting an air compressor in series to a calibrate nozzle that is able to regulate the air flow. By means of an empirical rule, the flow is translated into an objective pressure value.

A first objective of the present invention is to disclose an alternative to these known devices, which is able to take the form of a handheld compact aesthesiometer, which is portable.

Another objective of the present invention is an aesthesiometer that is accurate, able to blow pulses of air at different pressures and with a marked rectangular profile, meaning with a pressure value that is substantially constant during the puff, all of this without giving up the compactness of the aesthesiometer.

It is also of interest that the aesthesiometer be autonomous and not require a connection cable to the electrical grid. Then it is important that the mechanisms used to obtain and control the puffs of air do not require electrical compressing apparatuses, such as electrical motors, solenoids or another type of apparatus, with the purpose that the autonomy of the aesthesiometer, in anticipation of it requiring the use of batteries, is not compromised.

EXPLANATION OF THE INVENTION

The aesthesiometer object of the present invention is a handheld aesthesiometer comprising a gas lung, connected with intermediation from first valve means to a source of gas, the cited lung comprising an expandable cavity intended to house a volume of gas in a loading phase of the aesthesiometer; an outlet nozzle, connected to the gas lung with intermediation from second valve means, suitable for directing a puff of the volume of the gas housed in the gas lung in a firing phase of the aesthesiometer towards a target, for example a cornea of a patient; and a mechanism to ensure in the aforementioned firing phase of the aesthesiometer the release of the puff of the volume of gas contained in the gas lung in the direction of the outlet nozzle by means of a controlled contraction of the expandable cavity of the gas lung in order to ensure a substantially constant outlet pressure.

The aesthesiometer of the invention prevents the use of flow or pressure regulators in line with the gas supplying source which enables the aesthesiometer to be compact. Likewise, the gas lung enables the outlet pressure to be compressed to just a small volume of gas, enough to obtain the puff of gas to be expelled, significantly increasing the efficiency of the system in comparison with the known equipment. Likewise, the solution chosen to provide the puff with the required pressure can be miniaturised, small volumes of gas being involved. Furthermore, the use of an expandable cavity the contraction of which can be easily controlled mechanically enables puffs of air at a pressure that is substantially equal over time to be obtained in a simple and effective manner.

In a variant, the mechanism that ensures controlled contraction of the expandable cavity in the firing phase comprises elastic potential energy accumulation means, which accumulate potential energy from the effects of expansion of the expandable cavity during the loading phase of the aesthesiometer and which are able to release said potential energy in the firing phase of the aesthesiometer. Thus, the use of motor means, especially those that consume electricity, is not necessary to compress the volume of gas from which the puff of gas required to be fired is extracted.

Preferably, the elastic potential energy accumulation means comprise at least one constant-force spring which is stretched during the loading phase of the aesthesiometer and which all at once delivers a constant restoring force during the firing phase. This is a simple as well as effective way that contributes to obtaining puffs with a rectangular profile, meaning at a substantially constant pressure.

According to a variant of the invention, the expandable cavity has a movable wall and the mechanism comprises transmission means that mechanically link the movable wall and the elastic potential energy accumulation means, if it is the case made up of the constant-force spring. Advantageously, the spring or the potential energy accumulation means will not necessarily be arranged aligned with the direction of movement of the movable wall of the expandable cavity, which enables placement of the components in the aesthesiometer which favours the compaction thereof.

In a form of interest, the aforementioned transmission means comprise transmission by rack and pinion, the rack portion being joined to the movable wall of the expandable cavity and the pinion portion joined to the elastic energy accumulation means, all of this such that in the loading phase of the aesthesiometer, of inlet of gas into the expandable cavity coming from the source of pressurised gas, the expansion of said expandable cavity is produced by moving the movable wall thereof, in turn moving the rack portion in a first direction that ensures the rotation of the pinion portion around a rotation shaft and in a direction that loads the elastic potential energy accumulation means; and, in the firing phase of the aesthesiometer, upon connecting the expandable chamber to the outlet nozzle, the elastic energy accumulation means release the accumulated potential energy by applying a moment of force to the pinion portion which ensures the movement of the rack portion in a direction opposite from the first one and that produces the movement of the movable wall of the expandable cavity now in the direction of contraction thereof, expelling the puff of gas of the volume of gas accumulated therein during the loading phase.

According to an especially precise variant of the invention, the mechanism comprises a support body for the at least one constant-force spring, provided with a reel on which said spring is rolled/unrolled and a straight guide for guiding the movement of an actuating end of the spring by which it is joined to the pinion portion; and the joint between the aforementioned actuation end of the spring and the pinion portion, which determines the point of application of the restoring force that acts on this pinion portion in the firing phase of the aesthesiometer, is a joint that is movable in a guided manner in order to conserve the distance thereof with respect to the fixed rotation shaft of said pinion portion, thus ensuring that the restoring force applies a moment of force to the pinion portion with a substantially constant value.

The invention provides that at least one of the support body and the gas lung is mounted in the aesthesiometer with the ability to adopt different stable positions, each one offering a different distance from the point of application of the restoring force with respect to the rotation shaft of the pinion portion at the beginning of the firing phase.

According to a variant of interest, the first valve means allow for at least two operating positions, one of which is a closing position in which they impede communication between the source of gas and the gas lung; and the other is a loading position in which they enable communication between the source of pressurised gas and the gas lung, the aesthesiometer further comprising means for detecting the expansion measurement of the expandable cavity of the gas lung that are able to generate a governing signal of the first valve means so that these go from adopting the loading position to the closing position when the aforementioned expandable cavity reaches the expansion measurement corresponding to the predetermined volume of gas associated with the firing of the aesthesiometer and ending the loading phase.

This variant is advantageous compared to those in which the loading phase is stopped by a purely mechanical stop, for example, of the movable wall of the cavity with a path ending or any component of the mechanism 7 with a stop, which could produce an increase of the pressure of the gas in the cavity if it cannot expand, but it continues to supply gas from the source of pressurised gas. This fact could alter the good control of the outlet pressure.

The afore mentioned detection means can comprise an optical sensor.

The expandable cavity can be selected, preferably, from among a piston group; a bag or axial bellows.

The aesthesiometer can have a firing counter. The firing counter can count the number of times the detection means detect that the expandable cavity reaches the expansion measurement corresponding to the predetermined volume of gas sufficient for one puff or associated with the firing of the aesthesiometer.

The aesthesiometer can be equipped with a visual and/or audible indicator indicating that the number of times fired has reached a predetermined value.

As described sufficiently further on, the aesthesiometer is able to ensure, in the aforementioned firing phase, the release of a puff of the gas contained in the gas lung in the direction of the outlet nozzle in a time comprised between 0.3 s and 0.7 s, preferably between 0.4 and 0.6 s at an outlet pressure measured at 4 mm from the mouth of the outlet nozzle, according to a rectangular pulse of nominal value comprised between 0.0003 bar and 0.01 bar.

The invention contemplates that the source of gas is made up of a changeable cartridge of compressed medicinal gas.

Alternatively or complementary, it is envisaged that the aesthesiometer is equipped with an actuator for the controlled expansion of the expandable cavity, that via the first valve means enable the suction of ambient gas, in the form of air.

Said actuator for the controlled expansion of the expandable cavity moves a movable wall of said expandable cavity, said actuator being able to be manoeuvrable or motorised.

BRIEF DESCRIPTION OF THE DRAWINGS

and

DETAILED DESCRIPTION OF THE INVENTION

Figure 1:
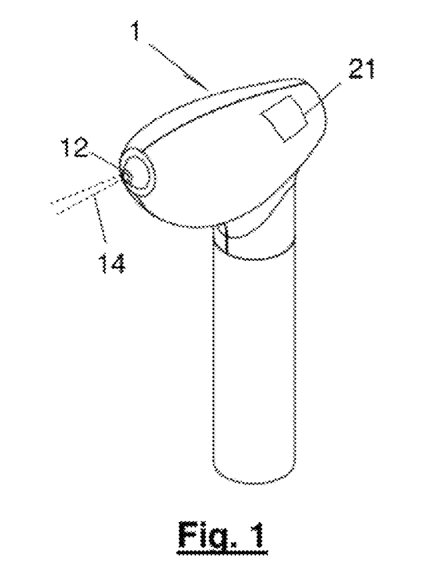
FIG. 1 is a general view of a handheld aesthesiometer according to the invention.
Figure 3:
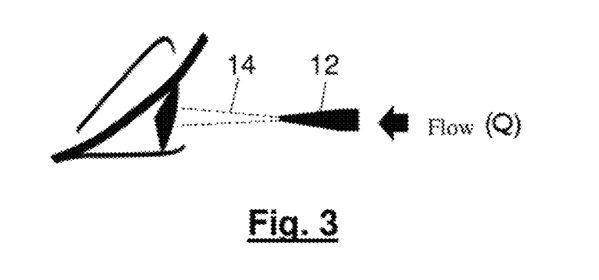
FIG. 3 illustrates the conventional application for which the aesthesiometer of the invention is intended.

FIG. 1 illustrates a handheld aesthesiometer 1 that exemplifies the invention. The aesthesiometer 1 has a general configuration in the form of a gun in which are distinguished a handle or grip-like portion and a main body in which an outlet nozzle 12 is arranged to direct puffs 14 of gas in the form of pulses, one pulse each time the aesthesiometer 1 is fired, in the direction of the cornea of a patient, as illustrated in FIG. 3.

Figure 2:
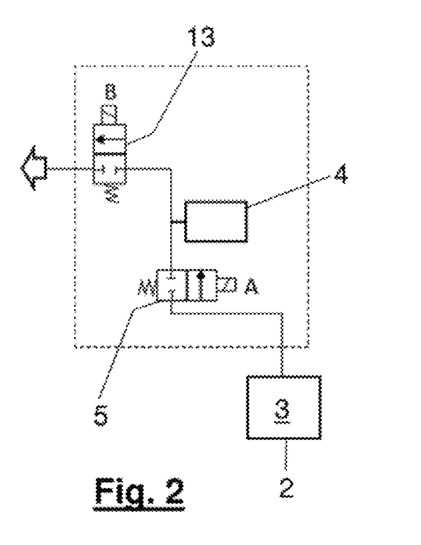
FIG. 2 is a basic diagram of the main components provided by an aesthesiometer according to the invention.

The diagram of FIG. 2 shows the main components of this version of the aesthesiometer and the relationship thereof. The aesthesiometer 1 comprises a gas lung 4 connected with intermediation from first valve means 5 to a gas source 2; and the outlet nozzle 12, connected to the gas lung 4 with intermediation from second valve means 13.

It is characteristic of the aesthesiometer 1 of the invention that the gas lung 4 comprises an expandable cavity 6 (see FIGS. 5 and 6a to 6c). This expandable cavity 6 is intended to receive in a loading phase of the aesthesiometer 1 a predetermined volume V1 of the gas 3 that will be supplied by the source 2 of the pressurised gas 3; and to expel in a firing phase a predetermined volume V2 of the gas 3 in the direction of the outlet nozzle 12 in a firing phase of the aesthesiometer 1, all of this as described in greater detail later on. Even though the volumes V1 and V2 can coincide, this will not necessarily always be the case since the gas balance must be taken into account given that there could be gas 3 housed in the expandable cavity 6 before starting the loading phase.

In the example, the source 2 of gas 3 is made up of a changeable cartridge 2a of compressed medicinal gas, specifically of air for clinical use of the type obtained by means of the compression of purified and filtered atmospheric air or of the oxygen and nitrogen mixture in proportions of 21% and 79% respectively, which are characterised in being free of particles, being bacteriologically apt, being free of oils and free of water. The storage volume of the cartridge can be comprised between 400-600 ml, and in order for the aesthesiometer to perform the function thereof, the pressure of the gas 3 can be approximately 5-7 bar. As explained below, other options, however, are contemplated to fill the expandable cavity 6 with gas.

The aesthesiometer 1 is equipped with a mechanism 7 that will ensure in the aforementioned firing phase of the aesthesiometer the release of the predetermined volume V2 of gas 3 to be expelled by means of controlled contraction of the expandable cavity 6 of the gas lung 4, specifically, controlled to ensure outlet pressure of the gas 3 in the outlet nozzle 12 that is substantially constant.

Figure 4:
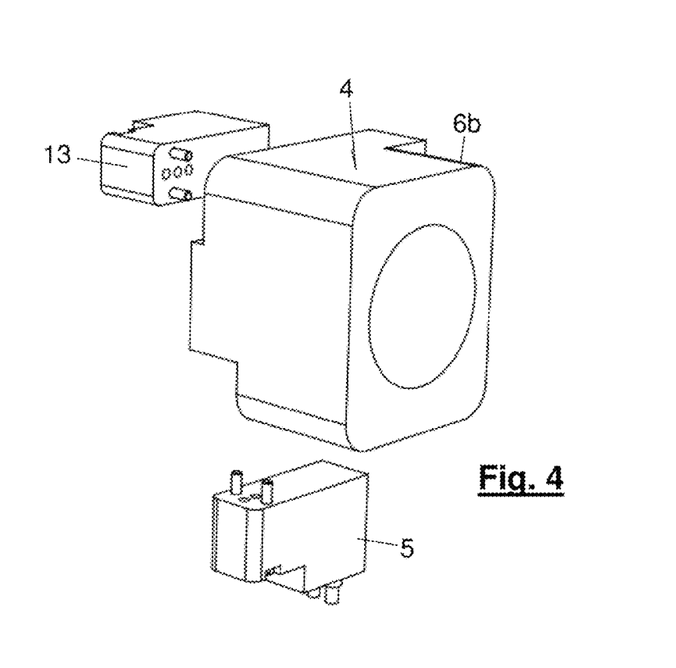
FIG. 4 shows the arrangement of the valve means and of an external casing or head of the gas lung according to a variant of an aesthesiometer according to the invention.

The expandable cavity 6 can be configured for example in the form of a piston, axial bellows or a bag. In the example of implementation of the invention, the expandable cavity 6 is the axial-bellows type and it has a movable wall 6a, linked to the mechanism 7. The expandable cavity 6 can be completely or partially housed in a rigid outer jacket or casing 6b, such as the one represented in FIG. 4, which can carry out the function of a connection head and in which the fluid connections can be formed with the first and second valve means 5 and 13 for supplying gas 3 to the expandable cavity 6 and for expelling gas 3 in the direction of the outlet nozzle 12, in the respective loading and firing phases of the aesthesiometer 1, all of this as illustrated in FIG. 4.

Figure 5:
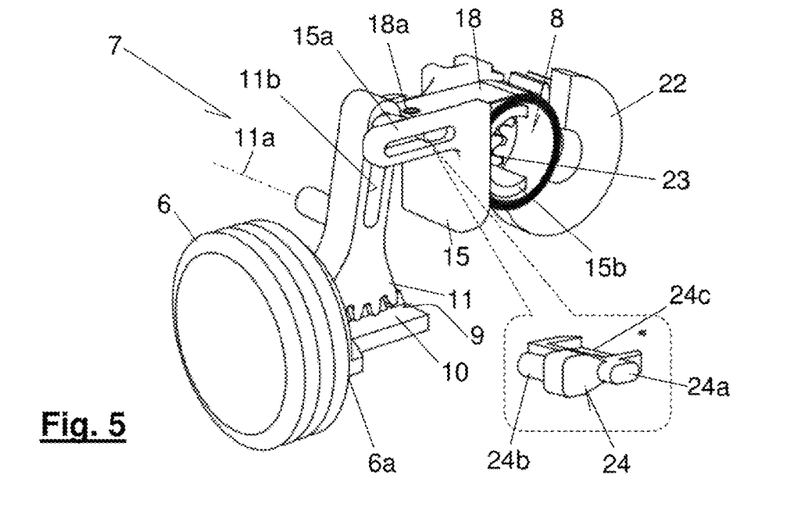
FIG. 5 is a perspective view of a suitable mechanism for ensuring the release of a predetermined volume of gas housed in an expandable cavity from the gas lung of the aesthesiometer by actuation of a movable wall thereof.

FIG. 5 shows in greater detail the assembly formed by the expandable cavity 6 (only partially shown) and the aforementioned mechanism 7, according to a variant of interest of the invention.

In this variant, for the controlled contraction of the expandable cavity 6 the mechanism 7 comprises elastic potential energy accumulation means 8 able to accumulate potential energy when the expandable chamber expands in a loading phase of the aesthesiometer, using the pressure of the entering gas 3 to do so, and releasing said potential energy in a firing phase of the aesthesiometer, which is taken advantage of in order to contract the expandable cavity 6 and expel a predetermined volume V2 of gas 3 stored inside of it.

This variant enables the gas to be driven without using motors or actuators that need a source of electrical current to do so, and at the same time they simplify the aesthesiometer and contribute to maintaining the manufacturing costs of this instrument at an acceptable level for the market.

In the example, the elastic potential energy accumulation means 8 are made up of a constant-force spring 18, which is deformed during the loading phase of the aesthesiometer and which instantly delivers a constant restoring force F (see FIG. 7) during the firing phase. This aspect is of interest because it will contribute to being able to expel a puff of gas 3 with a rectangular profile, meaning with a constant value or amplitude, through the outlet nozzle 12, this aspect being very important to be able to perform good diagnostics and obtain reliable results from the examination of a patient. La invention contemplates using more than one constant-force spring 18, as exemplified in FIG. 14, which will be referred to below.

The constant-force springs are a known and special variant of extension springs. In the example, this spring 18 is made up of a strongly rolled band of pre-hardened steel or stainless steel. Other possible materials are carbon steel or Inconel©.

In the example, the expandable cavity 6 has a movable wall 6a and the mechanism 7 comprises transmission means 9 that mechanically link this movable wall 6a and the constant-force spring 18.

These transmission means 9 comprise transmission by rack and pinion, the rack portion 10 being joined to the movable wall 6a of the expandable cavity 6 and the pinion portion 11 joined to the spring 18, specifically to an end actuation terminal 18a thereof.

The mechanism 7 has a support body 15 for the constant-force spring 18, provided with a reel 15b on which said spring is rolled/unrolled and a straight guide 15a to guide the movement of the aforementioned actuation end 18a of the spring by which it is joined to the pinion portion 11 of the transmission means 9.

The pinion portion 11 has, in the example, the form of a cantilever that can be rotated around a rotation shaft 11a, or fulcrum, fastened to the frame of the aesthesiometer 1. On one side of this rotation shaft 11a the cantilever is equipped with teeth for engaging with the rack portion 10 of the transmission means 9; and on the other side of the rotation shaft 11a the cantilever is joined to the actuation end 18a of the spring 8. Then, the linear movement of this actuation end 18a along the straight guide 15a in one direction or the other will apply a moment of force to the cantilever that will force it to rotate around the rotation shaft thereof 11a, and vice versa.

The invention provides a variant of the aesthesiometer 1 with high accuracy, which is chosen to ensure that the force applied on the movable wall 6a in the direction of contraction of the expandable cavity 6, driven by the restoring force of the spring 18, is substantially constant during the entire path of the actuation end 18a of the spring 18 during a firing manoeuvre.

Figure 7:
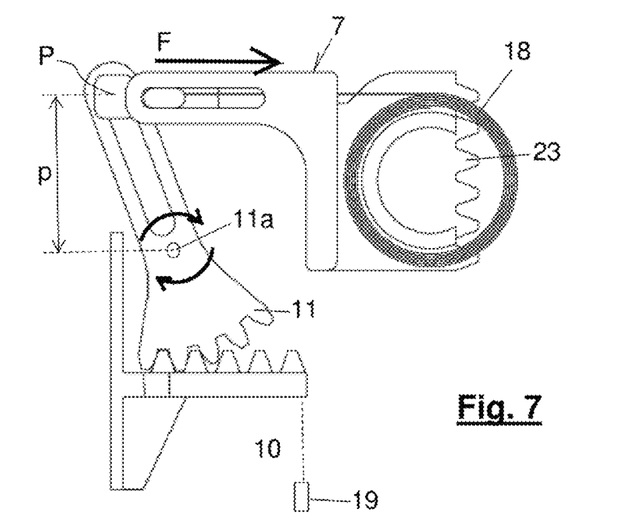
FIG. 7 is a schematic figure of the mechanism of FIG. 5.

With this goal, as shown in FIG. 7, in this perfected variant of the aesthesiometer 1 the joint between the aforementioned actuation end 18a of the spring 18 and the pinion portion 11, which determines the point of application P of the restoring force F which acts on this pinion portion 11 in the firing phase of the aesthesiometer, is a movable joint so that the distance p, which is the distance between the rotation shaft 11a of the pinion portion 11 and the straight portion on which the restoring force F rests, is always the same, in this way giving rise to a constant moment of force. To do so, the cantilever has a guide element or portion 11b along which a projection 24b provided by the connector 24 can slide, enlarged in FIG. 5, which links the actuation end 18a of the spring 18 with said cantilever. In the example, this connector 24 has a receiving portion in which the actuation end 18a of the spring 18 fits, joined firmly to this portion of the connector 24.

Figure 6A:
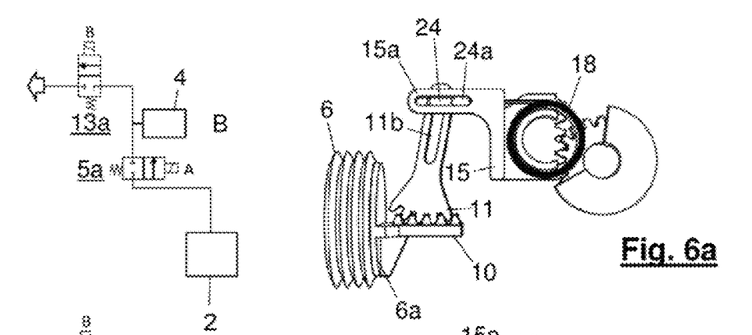
FIGS. 6a to 6c show a sequence of operations of the mechanism according to FIG. 5, each figure including a flow chart and a view of the mechanism in the state corresponding to it.

The operating principle of the aesthesiometer 1 is described below in reference to FIGS. 6a to 6c, and is as follows:

In the waiting situation B represented in FIG. 6a, the first valve means 5 adopt a closing position 5a in which they prevent communication between the source 2 of pressurised gas and the gas lung 4. Preferably, the second valve means 13 also adopt a closing position 13a in which they prevent the outlet of remaining gas 3 that may have been contained in the expandable cavity 6.

Figure 6B:
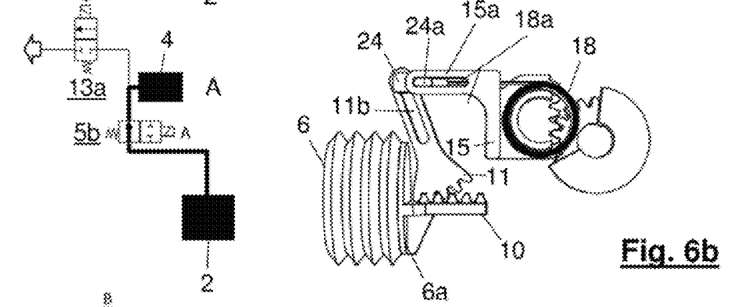

From this waiting situation B, of wanting to fire in the loading phase A illustrated in FIG. 6b, the valve means 5 are actuated so that they adopt a loading position 5b in which they enable communication between the source 2 of pressurised gas and the gas lung 4. In this loading phase A of the aesthesiometer 1, the inlet of gas 3 into the expandable cavity 6 coming from the source 2 of the pressurised gas produces the expansion of said expandable cavity 6 by moving the movable wall 6a thereof, in turn moving the rack portion 10 in a first direction that ensures the rotation of the pinion portion 11 around the rotation shaft 11a thereof and in a direction that stretches and loads the spring 18.

The invention envisages the aesthesiometer being equipped with detecting means 19 for detecting the expansion measurement of the expandable cavity 6 that are able to generate a governing signal of the first valve means 5 so that these go from adopting the loading position 5b to adopting the closing position 5a when the aforementioned expandable cavity 6 reaches the expansion measurement corresponding to a volume of gas that is sufficient to produce a puff with a predetermined volume V2 of gas 3 to be expelled associated with the firing of the aesthesiometer and ending the loading phase A.

Figure 6C:
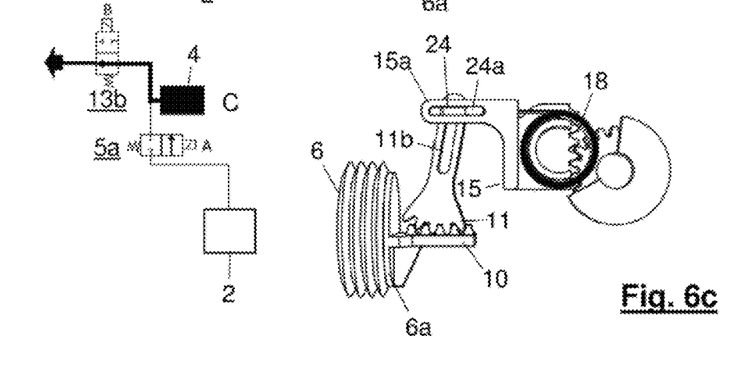

A firing phase C of the aesthesiometer represented in FIG. 6c will then start, preferably automatically although it is envisaged that it can also be in response to an action of the user.

To do so, the second valve means 13 are activated so that these can go from adopting the closing position 13a to adopting a firing position 13b during a pre-established period of time, for example, 0.5 s.

For this case, the second valve means 13, and naturally the first valve means 5 as well, can be electronic and the aesthesiometer 1 can be equipped with a factory-calibrated timer for an opening time of the second valve means 13 of 0.5 s or alternatively be equipped with other means that can be configured or selected by the user, such as a screen and an assembly of buttons that enables the user to select the duration of the puff of gas during the firing phase C, or a free value or a value from a list of values previously programmed in the factory.

Once the second valve means 13 adopt the firing position 13b, almost instantaneously the spring 18 releases the accumulated elastic potential energy and applies a restoring force F on the pinion portion 11 of the transmission means 9 which ensures the movement of the rack portion 10 that in turn produces the movement of the movable wall 6a of the expandable cavity 6 now in the direction of contraction thereof, expelling a predetermined volume V2 of gas 3 to be expelled from the gas 3 accumulated therein in the loading phase A.

The firing action will be interrupted by the action of the valve means 13 when these once again adopt the closing position 13a thereof, which will occur once 0.5 s have passed, in the example.

The aesthesiometer 1 will then be in the waiting position B again, illustrated in FIG. 6a.

An aesthesiometer is a device that is used to evaluate perceptive sensitivity. In order for the aesthesiometer 1 to be able to deploy all the functions thereof, it is essential that it be prepared to fire puffs of air at different pressures.

In the mechanism 7 of the aesthesiometer 1 of the example, the value of the moment of force is M (see FIG. 7)

$$M = F*p$$

will be able to vary if the distance p is modified. Taking advantage of this principle, according to another aspect of the aesthesiometer 1 of the invention, it is envisaged that at least one of the support body 15 or the gas lung 4 is mounted in the aesthesiometer with the ability to adopt different stable positions, each one offering a different distance p at the start of a firing phase C.

In the aesthesiometer 1 of the example, the first alternative is chosen, meaning that the support 15 is mounted in the aesthesiometer, being able to adopt different positions with respect to the gas lung 4, more specifically with respect to the expandable cavity 6. This characteristic is the one shown in FIGS. 8a and 8b, FIG. 8a corresponding to a position with maximum stimulus and FIG. 8b to a position with minimum stimulus.

Figure 8A:
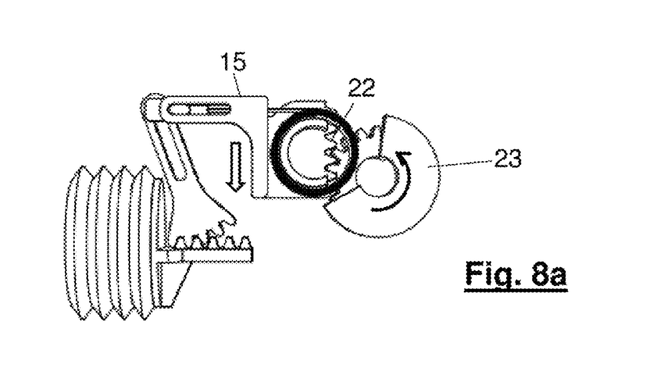
FIGS. 8a and 8b show the mechanism of FIG. 5 adopting the elastic potential energy accumulation means in different positions with respect to the expandable cavity.
Figure 8B:
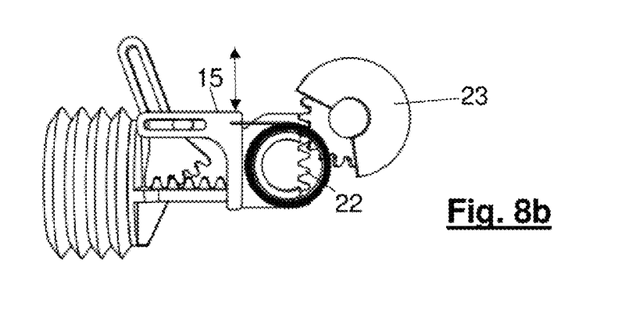

In the form represented, the support 15 and with it the constant-force spring 18 are mounted and guided in the aesthesiometer 1, the relative position thereof being able to be changed with respect to the expandable cavity 6 by means of actuation 23 here in the form of a wheel that meshes with corresponding teeth 22 that are provided in the support 15. The wheel can be actuated by digital pressure, meaning manually, by a user, and the aesthesiometer 1 can be provided with elastic means for fitting with the wheel or with the support 15 in order to equip these with different stable positions, each one of these will correspond to a firing of a puff of gas 3 at a different outlet pressure.

There are several parameters that can be adjusted in order to obtain puffs of air with pressures of interest. Different tests were performed, altering, for example, the volume of gas 3 introduced into the expandable cavity 6 in a loading phase A and/or the initial angular position of the pinion portion 11 of the mechanism 7 and/or the distance p and/or the volume of gas 3 initially present in the expandable cavity 6 and/or the distance p (finally choosing to equip the aesthesiometer with up to 5 different positions for the support 15 with respect to the expandable cavity 6) and/or the characteristics of the constant-force spring 18, among other parameters that enable an adjustment in the response of the aesthesiometer 1, and they have enabled an optimal design of a handheld aesthesiometer 1 with the features shown in Tables 1 and 2 below.

TABLE 1

Parameters of the aesthesiometer for each one of the 5 different air puff options.

| Position | Puff duration | Q (ml/ min) | Mass flow (kg/s) | outlet speed (m/s) | Pressure in the target (*)(bar) | Force (mN) | Gas pressure in the cavity (bar) |
|---|---|---|---|---|---|---|---|
| 5 | 0.5 | 410 | 9.00E−06 | 40 | 0.0086 | 0.26 | 0.0196 |
| 4 | 0.5 | 315 | 6.88E−06 | 31 | 0.0050 | 0.158 | 0.01214 |
| 3 | 0.5 | 254 | 5.54E−06 | 25 | 0.0032 | 0.106 | 0.00829 |
| 2 | 0.5 | 180 | 3.92E−06 | 18 | 0.0015 | 0.056 | 0.00458 |
| 1 | 0.5 | 102 | 2.21E−06 | 10 | 0.00046 | 0.019 | 0.00178 |

(*) values measured at a distance of 4 mm from the outlet nozzle of the aesthesiometer.

TABLE 2

Parameters of the aesthesiometer for each one of the 5 different air puff options.

| Position | Puff duration (s) | Volume of the puff (mm³) | Movement of the wall of the cavity (mm) |
|---|---|---|---|
| 5 | 0.5 | 3.4 | 5.6 |
| 4 | 0.5 | 2.7 | 4.6 |
| 3 | 0.5 | 2 | 3.5 |
| 2 | 0.5 | 1.5 | 2.5 |
| 1 | 0.5 | 0.84 | 1.4 |

In addition to the versatility that the aesthesiometer 1 offers, capable of firing several puffs of air with different magnitudes, the circumstance arises that these puffs follow a rectangular profile, with a substantially constant nominal value, improving this aspect as well with respect to other aesthesiometers documented in the state of the art.

Figure 9:
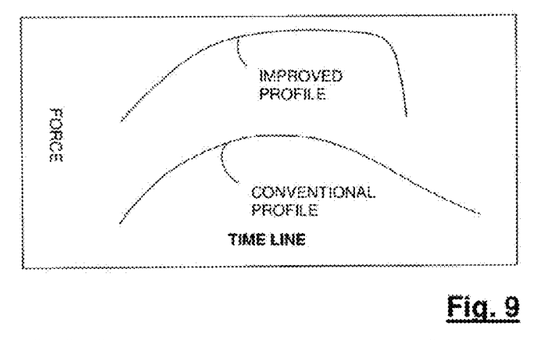
FIG. 9 shows the profile of corresponding puffs of gas that are obtained with documented aesthesiometer equipment in the state of the art.

FIG. 9, an extract from patent document WO9317613, exemplifies the profile over time of the puffs of air able to be obtained by means of known aesthesiometer equipment, the upper profile corresponding to that of an aesthesiometer that presumably perfected the known techniques.

Figure 10:
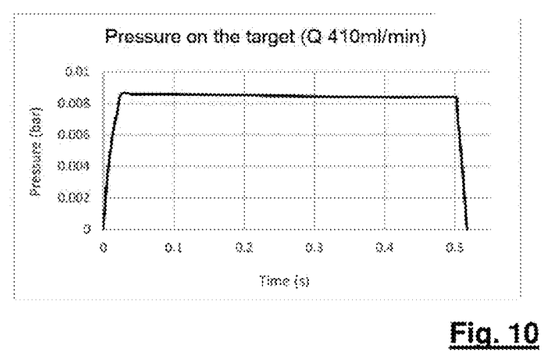
FIGS. 10 and 11 show the profile of corresponding puffs of gas that are obtained with an aesthesiometer object of the present invention.
Figure 11:
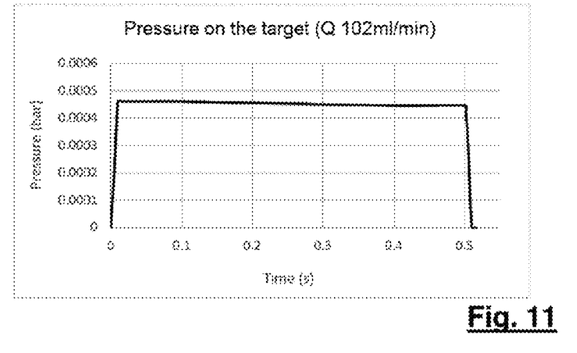

In contrast to these profiles, FIGS. 10 and 11 show the profile of corresponding puffs of gas that are obtained with the aesthesiometer object of the present invention, for an objective pressure of 0.0086 bar and 0.00046 bar, respectively. Note the rectangular profile that these puffs show and especially how the pulses of gas are obtained with a substantially constant pressure value.

In the variant of the aesthesiometer 1 of the invention wherein the gas 2 source is in the form of a changeable cartridge, said cartridge can be housed in the portion configured as a handle while the main components, marked with a dotted line in the diagram of FIG. 2, can be housed in the main body of the aesthesiometer 1.

The recharging of the cartridge of pressurised gas 3 can be as simple as the conventional manoeuvre of replacing a battery in any electronic device. However, the invention provides the aesthesiometer with a firing counter with the goal of estimating when the cartridge will be close to running out and being able to perform preventative maintenance of the aesthesiometer.

Taking advantage of the fact that the aesthesiometer can be equipped with the detection means 19, in one variant of the invention the firing counter counts the number of times that these detection means 19 detect that the expandable cavity 6 reaches the predetermined volume of gas 3 associated with firing the aesthesiometer once. In other words, the counter counts the number of times that a loading phase A has been completed, thereby making it possible to estimate the volume of gas 3 that has been extracted from the cartridge.

Knowing the gas 3 capacity that the cartridge has, it does not have a greater problem of equipping the aesthesiometer with a visual and/or audio indicator 21 indicating that the number fired has reached a predetermined value, warning that the cartridge exchange should be performed.

Figure 12:
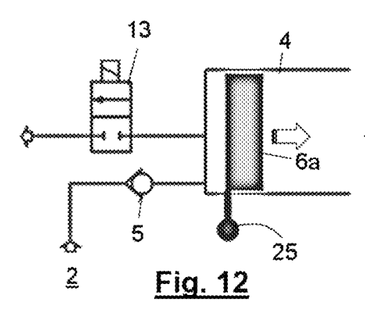
FIGS. 12 and 13 are corresponding basic diagrams of the main components of respective variants of an aesthesiometer according to the invention.
Figure 13:
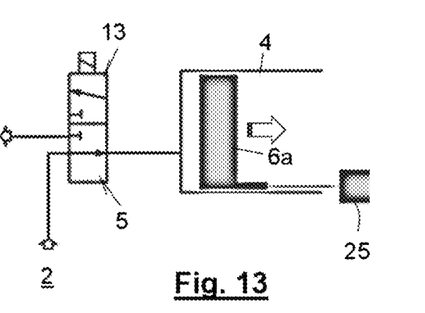

The diagrams of FIGS. 12 and 13 show alternative variants of an aesthesiometer according to the invention, such that it refers to supplying gas 3 to the expandable cavity 6.

In these variants, instead of using a cartridge 2a as a source 2 of gas 3, the aesthesiometer is equipped with an actuator for the controlled expansion 25 of the expandable cavity 6 that via the first valve means 5 enable the suction of ambient gas, in the form of air.

The actuator for the controlled expansion 25 of the expandable cavity 6 moves a movable wall 6a of said expandable cavity 6, said actuator being able to be manoeuvrable, that is to say, manually actuated, as illustrated by FIG. 12; or motorised, for example, by means of a solenoid device, as illustrated by FIG. 13.

The operating principle of the aesthesiometer is the same as that described previously, with the difference that, from the waiting situation B, of wanting to fire in the loading phase, the valve means 5 are actuated so that they enable communication between the source 2 of gas and the gas lung 4, the source 2 of gas, however, now being the ambient air. In the loading phase of the aesthesiometer, the inlet of gas into the expandable cavity 6 is produced by suction, caused by the movement of the movable wall 6 of the expandable cavity by means of the actuator for the controlled expansion 25 of the expandable cavity 6 referred to previously, in the direction indicated by the arrows in FIGS. 12 and 13.

Like in the version of the aesthesiometer equipped with a cartridge 2a of pressurised gas 3, the movement of the movable wall 6a, by means of the transmission means 9, stretches and loads the elastic potential energy accumulation means 8.

Figure 14:
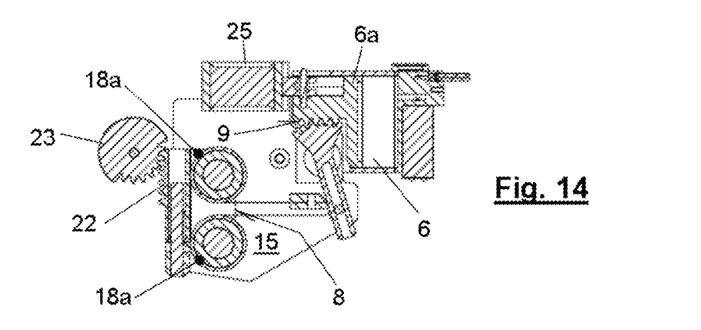
FIG. 14 shows according to a longitudinal cutting plane another variant of an aesthesiometer according to the invention, specifically, of the mechanism for ensuring the release of a predetermined volume of gas housed in the expandable cavity.
Figure 15A:
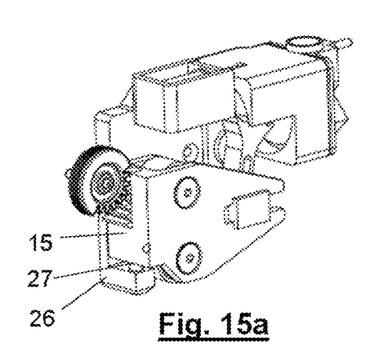
FIGS. 15a and 15b show the mechanism of FIG. 14 adopting the elastic potential energy accumulation means in different positions with respect to the expandable cavity.
Figure 15B:
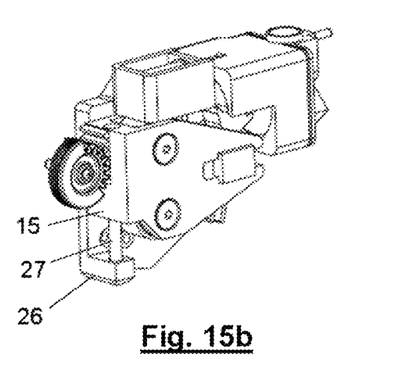

FIG. 14 illustrates an aesthesiometer 1 that implements the solution illustrated in the diagram of FIG. 13, equipped with an actuator for the controlled expansion 25 of the motorised expandable cavity 6, in the form of a solenoid device. In this version it should be noted that the elastic potential energy accumulation means 8 comprise in this case two constant-force springs 18, 18' that act in parallel on the transmission means 9, in the others that are analogous to those of the version of the aesthesiometer with a single constant-force spring. This version of FIG. 14 is also used to show that the invention contemplates that the assembly formed by the main components of the aesthesiometer, correctly assembled, is self-supporting. For this purpose, the same is provided with a sort of frame or base plate 26 to which the support body 15 of the elastic potential energy accumulation means 8 is coupled with the capacity of guided movement, such that said support can adopt, with respect to the transmission mechanism 9, the different positions that enable modulating the force transmitted by the elastic potential energy accumulation means 8 to the movable wall 6a of the expandable cavity 6, firmly fixed to the cited frame or base plate 26. This feature is the one shown in FIGS. 15a and 15b, FIG. 15a corresponding to a position with maximum stimulus and FIG. 15b to a position with minimum stimulus.

The guided movement referred to previously is implemented, in these examples, by means of a guide and pin set, specifically by means of a pin in the form of a straight rod 27, joined to the frame or base plate 26 oriented normally to the core of the springs 18, 18', inserted with adjustment into a hole that is provided to the support body 15 such that said body can slide along the rod.

The invention claimed is:

1. A handheld aesthesiometer, comprising
   a gas lung, connected with intermediation from first valve means to a source of gas, comprising an expandable cavity intended to house a volume of the gas in a loading phase of the aesthesiometer;
   an outlet nozzle, connected to the gas lung with intermediation from second valve means, suitable for directing a puff of the volume of the gas housed in the gas lung in a firing phase of the aesthesiometer towards a target and
   a mechanism configured to ensure, in the aforementioned firing phase of the aesthesiometer, a release of the puff of the volume of gas housed in the gas lung in a direction of the outlet nozzle by means of a controlled contraction of the expandable cavity of the gas lung in order to control outlet pressure;
   wherein said mechanism comprises an elastic potential energy accumulation means and wherein the elastic potential energy accumulation means comprise at least one constant-force spring which is stretched during the loading phase of the aesthesiometer and which all at once delivers a constant restoring force during the firing phase.

2. The aesthesiometer according to claim 1, wherein said elastic potential energy accumulation means is configured to accumulate potential energy from an effect of an expansion of the expandable cavity during the loading phase of the aesthesiometer and wherein the elastic potential energy accumulation means is configured to release said potential energy in the firing phase of the aesthesiometer.

3. The aesthesiometer according to claim 2, wherein the expandable cavity has a movable wall and the mechanism comprises transmission means that mechanically link the movable wall and the elastic potential energy accumulation means, and wherein the elastic potential energy accumulation means is configured to be stretched during the loading phase of the aesthesiometer and deliver the constant restoring force during the firing phase.

4. The aesthesiometer according to claim 1, wherein the first valve means enable at least two operating positions,
   a closing position which impedes communication between the source of gas and the gas lung; and
   a loading position which enables communication between the source of gas and the gas lung, the aesthesiometer further comprising means for detecting an expansion measurement of the expandable cavity of the gas lung during the loading phase and generating a governing signal of the first valve means that causes the first valve means to go from adopting the loading position to adopting the closing position when the expandable cavity reaches an expansion measurement corresponding to a predetermined volume of gas associated with the firing of the aesthesiometer and ending the loading phase.

5. The aesthesiometer according to claim 4, wherein the means for detecting comprise an optical sensor.

6. The aesthesiometer according to claim 1, wherein the expandable cavity is selected from among a piston; a bag or axial bellows.

7. The aesthesiometer according to claim 1, further comprising a visual and/or audible indicator that indicates that a number of times fired has reached a predetermined value.

8. The aesthesiometer according to claim 1, wherein the mechanism is configured to release the puff of the gas contained in the gas lung in a time between 0.3 s and 0.7 s.

9. The aesthesiometer according to claim 1, wherein, in the firing phase, the aesthesiometer is configured to directed the puff of the volume of the gas at an outlet pressure, such that the outlet pressure is between 0.0003 bar and 0.01 bar at a distance 4 mm from a mouth of the nozzle according to a rectangular pulse of nominal value.

10. The aesthesiometer according to claim 1, wherein the source of gas is made up of a changeable cartridge of compressed medicinal gas.

11. The aesthesiometer according to claim 1, further comprising an actuator for controlled expansion of the expandable cavity, that via the first valve means enable suction of ambient gas, in a form of air.

12. The aesthesiometer according to claim 11, wherein the actuator for the controlled expansion of the expandable cavity moves a movable wall of said expandable cavity, said actuator being able to be manoeuvrable or motorised.

13. The aesthesiometer according to claim 1, wherein the mechanism is configured to release the puff of the gas contained in the gas lung in a time between 0.4 s and 0.6 s.

14. A handheld aesthesiometer, comprising
   a gas lung, connected with intermediation from first valve means to a source of gas, comprising an expandable cavity configured to house a volume of the gas accumulated in a loading phase of the aesthesiometer;
   an outlet nozzle, connected to the gas lung with intermediation from second valve means configured to direct a puff of the volume of the gas housed in the gas lung in a firing phase of the aesthesiometer towards a target and
   a mechanism configured to ensure, in the firing phase of the aesthesiometer, a release of the puff of the volume of gas housed in the gas lung in a direction of the outlet nozzle by a controlled contraction of the expandable cavity of the gas lung to control outlet pressure;
   wherein said mechanism comprises elastic potential energy accumulation means configured to accumulate potential energy from an expansion of the expandable cavity during the loading phase of the aesthesiometer and wherein the elastic potential energy accumulation means is configured to release said potential energy in the firing phase of the aesthesiometer;
   wherein the expandable cavity has a movable wall and the mechanism comprises transmission means configured to mechanically link the movable wall and the elastic potential energy accumulation means;
   wherein the elastic potential energy accumulation means is configured to be stretched during the loading phase of the aesthesiometer and is configured to deliver a constant restoring force during the firing phase;
   wherein the transmission means comprise a rack and a pinion, the rack being joined to the movable wall of the expandable cavity and the pinion joined to the elastic energy accumulation means; and
   wherein:
      in the loading phase of loading the volume of gas into the expandable cavity, the movable wall is configured to move and produce the expansion of said expandable cavity, the rack is configured to move in a first direction, and the pinion is configured to rotate around a rotation shaft in a direction that stretches the elastic potential energy accumulation means and loads the volume of the gas into the expandable cavity; and
      in the firing phase, upon connecting the expandable cavity to the outlet nozzle, the elastic energy accumulation means is configured to apply a moment of force to the pinion, the rack is configured to move in a direction opposite from the first direction to release the accumulated potential energy, and the movable wall is configured to move in a direction of contraction of the expandable cavity to expel the puff of the volume of gas loaded in the expandable cavity during the loading phase.

15. The aesthesiometer according to claim 14, wherein the elastic potential energy accumulation means comprise a constant-force spring configured to be stretched during the loading phase of the aesthesiometer and all at once deliver the constant restoring force during the firing phase; and
   wherein the mechanism further comprises:
      a support body for the constant-force spring, the support body being provided with a reel on which said constant-force spring is rolled/unrolled and a straight guide configured to guide movement of an actuation end of the constant-force spring; and
      a joint between the actuation end of the constant-force spring and the pinion, wherein the joint is configured to join the actuation end to the pinion and defines a point of application of the constant restoring force that acts on the pinion in the firing phase of the aesthesiometer, the joint being configured to move in a guided manner to conserve a distance thereof with respect to the rotation shaft of said pinion, and wherein movement of the joint in the guided manner is configured to ensure that the constant restoring force delivered by the constant-force spring applies the moment of force to the pinion.

16. The aesthesiometer according to claim 15, wherein at least one of the support body or the gas lung is mounted in the aesthesiometer and is configured to adopt different stable positions and provide an effect of:
   a) a different distance of the point of application of the constant restoring force with respect to the rotation shaft of the pinion at a beginning of the firing phase; or
   b) a different stretching magnitude of the constant-force spring at the beginning of the firing phase.

* * * * *